United States Patent [19]

Bartlett

[11] Patent Number: 5,423,791
[45] Date of Patent: Jun. 13, 1995

[54] VALVE DEVICE FOR MEDICAL FLUID TRANSFER

[76] Inventor: J. Mark Bartlett, 11518 Lochlynn Cir., Dallas, Tex. 75228

[21] Appl. No.: 4,704

[22] Filed: Jan. 14, 1993

Related U.S. Application Data

[63] Continuation-in-part of Ser. No. 861,275, Mar. 31, 1992, abandoned.

[51] Int. Cl.⁶ .............................................. A61J 1/00
[52] U.S. Cl. ..................... 604/403; 406/90; 406/91
[58] Field of Search ............... 604/403, 415, 905, 89, 604/90, 91; 251/334, 336, 903

[56] References Cited

U.S. PATENT DOCUMENTS

| | | | |
|---|---|---|---|
| 2,764,157 | 9/1956 | Oliva et al. | 64/415 X |
| 3,477,431 | 11/1969 | Walecka | 604/89 |
| 4,379,458 | 4/1983 | Bauer et al. | 604/905 X |
| 4,457,709 | 7/1984 | Bellotti et al. | 604/905 X |
| 4,470,520 | 9/1984 | Sullivan | 604/403 X |
| 4,506,691 | 3/1985 | Tseo | 406/91 X |
| 4,713,054 | 12/1987 | Kelly et al. | 604/89 |

*Primary Examiner*—Sam Rimell
*Attorney, Agent, or Firm*—Henry Croskell

[57] ABSTRACT

A valve device for medical fluid transfer and methodology utilizing the valve device provides a multi-purpose needle free valve assembly and bottle or IV port adapters for multiple medical use requirements. The adapters being suitable for insertion into IV ports, medicine bottles or vials and IV luer lock connectors. The valve device assembly for fluid transfer is used within administration structures for medical purposes utilizing a needle free syringe as the transfer apparatus, the needle free syringe being mateable with the valve device assembly in a first connector and when inserted, the syringe tip opens the valve by compression of the valve head or piston and valve springs allowing for two-way communication between the barrel of the needle free syringe and the IV ports, medicinal bottles or vials and IV luer lock connectors.

23 Claims, 4 Drawing Sheets

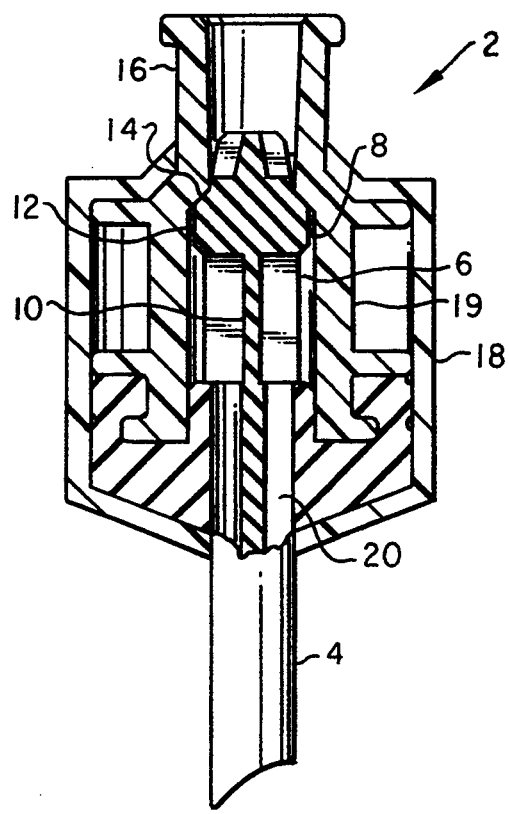
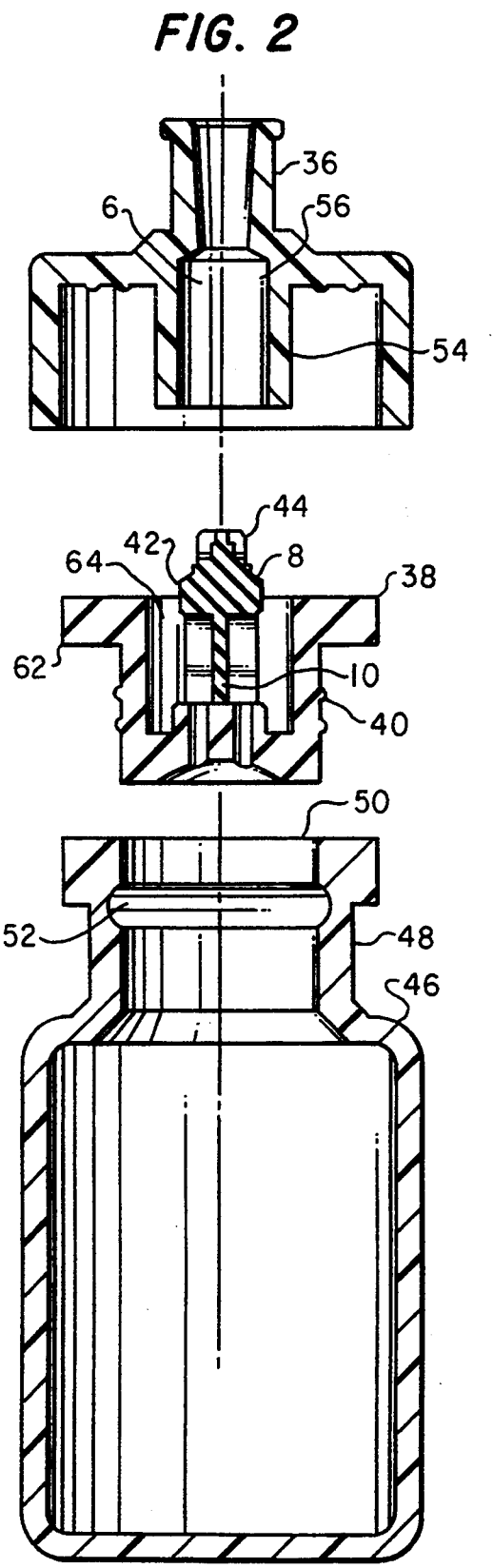
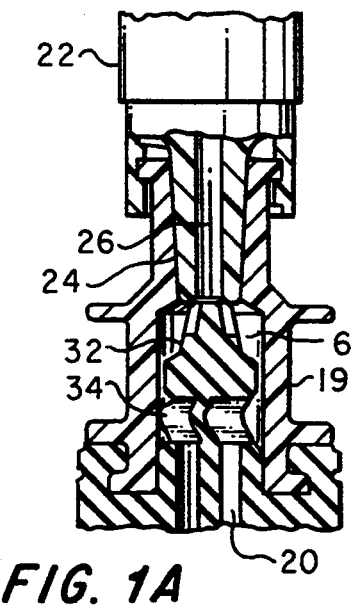
FIG. 1
FIG. 2
FIG. 1A

VALVE DEVICE FOR MEDICAL FLUID TRANSFER

CROSS-REFERENCE TO RELATED APPLICATION

This is a continuation-in-part of patent application Ser. No. 07/861,275, filed Mar. 31, 1992, entitled "Bartlett Adapter", now abandoned.

BACKGROUND OF THE INVENTION

The present invention relates to a needle free valve device or adapter for use with fluid flow and administration structures for medical purposes.

In another aspect the present invention relates to the multi-purpose needle free valve device which is adaptable to multiple medical use requirements, said adapter being suitable for insertion into IV ports, medicine bottles or vials and IV luer lock connectors. In still another aspect, the invention relates to a method of obtaining fluid medicines from medical vials and delivering said medicines to, for example, IV ports, through use of needle free transfer systems having the adapter valve device in place.

Over the years a wide variety of devices and methods have been developed to assist the health care practitioner in delivering medications as well as the taking of body fluids. In more recent times, a wide variety of devices and methods have been developed to not only assist the health care practitioner but to protect the health care practitioner as well as patients from needle sticks. However the need remains for adapter valve devices for use in fluid flow and the transfer of fluids from medicinal containers to IV ports and other administrative structures for medical purposes.

Aside from the hazards of needle sticks both to the health care practitioner and the patient from normal needle syringe transfer means from medicinal vials to, for example, IV ports, is the common problem of known valves utilized in administrative structures for medical purposes of reversal of fluid flow or liquid flow through tubing due to back pressure or leakage of the valve when mounted and utilized with a medicinal container such as a bottle or vial. The needle free valve device for medical fluid transfer can accomplish these multiple purpose health care procedures which will enable health care professionals especially trained in performing patient care to obtain the necessary quantity of medicinal volumes in an uncontaminated state from a manufacturer's container and transferring said quantity of medicinal fluid to an IV port without the use of needles or the hazard or danger of leakage of the device valve in either direction, i.e. leakage of the fluid from the IV due to back pressure or leakage of medicinal fluid from the vial or bottle.

The valve adapter device is a multiple purpose adapter having a valve means positioned in the closed position by spring means, however, said spring means being overridden by insertion of a needleless syringe tip against the valve, overcoming the spring load thus opening the valve. The valve device can be used to push IV medicinal fluids into the IV system, fit into medicinal bottles or vials to act as a channel between the medicinal bottle and needleless syringe for obtaining the medicinal fluids from the bottle as well as utility in place of, for example, a heparin lock. The needle free valve device can be opened and closed to inject medicinal fluids or withdrawal of body fluids. The valve device has different advantages in order to accommodate various uses either in supplier medicinal containers and/or hospital settings. The valve device adapters eliminate needle usage while drawing medications and while injecting medications through an IV port.

Accordingly, since it is a common practice to utilize needle syringe devices to extract medicinal fluids from bottles or vials in order to transfer said medicinal fluids to an IV port and injection therein, said systems remain silent with respect to a needle free valve device accomplishing the same objectives of fluid transfer. There remains a continuing need to provide such a needle free valve device and methodology which not only benefits the heath care practitioner but the overall health care environment inclusive of contaminated needle devices, thus avoiding risk of infection to both patient and health care practitioner.

SUMMARY OF THE INVENTION

An object of the present invention is to provide a needle free valve device which is adaptable to use in transfer of medicinal fluids from normally rubber membrane enclosed containers to normally rubber membrane enclosed IV ports requiring needle-type syringe transfer. Another object of the present invention is to provide valve device adapters for medicinal fluid containers and IV ports which eliminate the need of needle insertion for opening a communication chamber between the needle free syringe, bottle or container and/or the IV.

And yet another object of the present invention is to provide a valve means which is normally closed and which can very quickly be opened and as quickly be closed to prevent back flow of liquid from the IV system or leakage from the IV system and/or medicinal fluid container.

The valve device with adaptations for injecting medicinal fluids into IV lines performs as a port for reception of numerous medicinal fluids and can also be adapted to act as a connection between medicinal bottles and needle free syringes to expedite medicinal fluid removal from medicinal fluid bottles or containers. A single valve device can be provided with a universal female adapter at an exterior portion and the interior of the adapter having an open passage way which is either open or blocked by a valve means. Said valve means having a spring pressure to hold the valve in a closed position but being subject to opening by insertion of a needle free syringe tip or other means. Medicinal fluids can be transferred from needle free syringes inserted into the valve device thereby opening the valve permitting open communication between the syringe and the receptive medical apparatus such as an IV port or container. The valve device can provide in an open position a receptive channel for body fluids aspirated from needle free syringes. Different adaptations of the valve device allows for different uses in the hospital or medical setting required in the drawing of medications and injections of medications through IV ports as well as withdrawal of body fluids from tubing and injection of said body fluids into a container for laboratory analysis.

Advantages and novel features of the invention will be set forth in part in the description which follows and will become apparent to those skilled in the art upon examination of the following or may be learned by practice of the invention. The objects and advantages of the invention may be obtained by means of the combinations particularly pointed out in the appended claims, including equivalence. Details of construction and operation are more fully hereinafter described and claimed with references being to the accompanying drawings forming a part hereof, wherein like numerals refer to like parts throughout.

BRIEF DESCRIPTION OF THE DRAWINGS

The inventive valve device for medicinal fluid transfer may be more fully understood by reference to the accompanying drawings wherein:

FIG. 1 is a longitudinal cross-sectional view through the valve device with the valve in closed position and with an adapter tube for puncture entry into membrane IV port or bottle covers;

FIG. 1A is a partial cross-sectional view of another embodiment of the valve device with the valve in an open position due to contact with a needle free syringe tip projection;

FIG. 2 is an exploded cross-sectional view of the valve device with an adapter suitable for affixing to a bottle opening or throat;

DETAILED DESCRIPTION OF THE INVENTION

Figure 5:
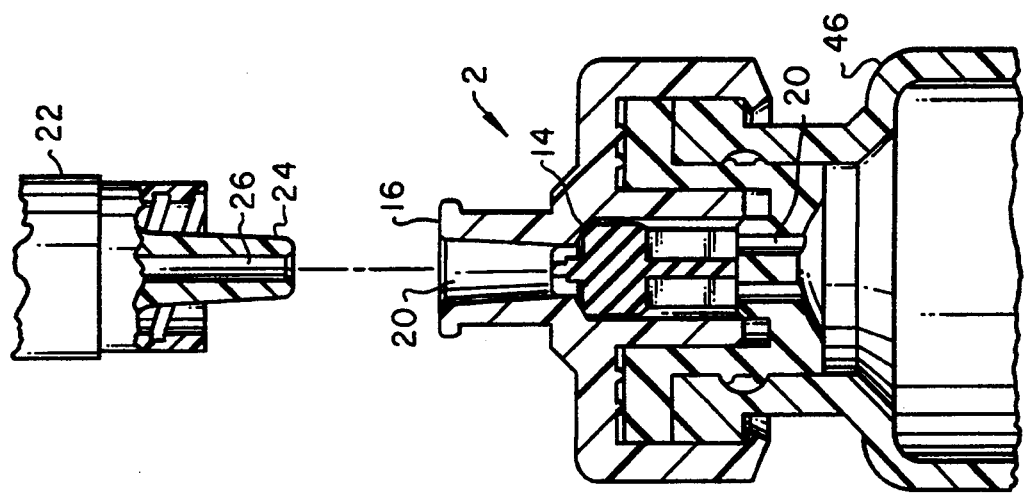
FIG. 5 is an exploded cross-sectional view of the needle free syringe tip and the assembly of FIG. 4 with the syringe tip positioned for insertion into the valve device.

Preferred embodiments of the needle free valve device for use with fluid flow within administration structures for medical purposes as well as methods of use of the valve device are presented only with those components of primary interest with respect to the device apparatus and method. The drawings do not illustrate all of the mechanical elements for use of or control of the various components of the apparatus. These omitted elements have various known forms which can be readily realized by one of normal skill in the art having knowledge of the information provided herein with regard to the mode of operation of the valve device and the various components and related methods utilized for transfer of medicinal fluids through use of a needle free syringe or other needle free means.

Referring to the drawings, FIGS. 1 and 1A present a longitudinal cross-sectional view through the valve device with a valve in closed position, FIG. 1, and with an adapter tube for puncture entry into membrane enclosed medical fluids. In FIG. 1A the partial cross-sectional view of the valve device with the valve in an open position due to contact with a needle free syringe tip projection which allows for open communication between the syringe and either a medicinal fluid container or IV port.

One embodiment of the needle free valve device is shown in FIG. 1 wherein the valve device 2 is adapted with an adapter tube 4 for puncturing membrane sealed IV ports or medicinal vial covers. The adapter tube 4 is hollow and communicates through open communication with valve chamber 6 which is closed at an opposite end of the chamber from the adapter tube 4 entry by valve 8. A valve spring means 10 holds valve 8 in the closed position 12 against valve seat 14. The valve device 2 has a valve female connector 16 which is part of or connected to outer valve housing 18. The valve device 2 has an inner valve housing 19 which defines the valve chamber 6. The valve chamber 6 is in open communication with passage 20 which continues through the adapter tube 4 for open communication from inside a punctured membrane (not shown) with the valve chamber 6.

In FIG. 1A, a partial cross-sectional view of another embodiment of the valve device 2 is shown with the valve in open position due to contact with needle free syringe 22 male tip 24 which is inserted into the valve device female connector 16. The needle free syringe male tip having a passage 26 in communication with the bore of the syringe 22 and valve chamber 6 with valve 8 in open position 32. The valve 8 having valve spring means 10 when in the valve open position 32 is the result of the valve spring compaction 34 thereby providing open communication between the syringe, valve chamber 6 and passage 20 which can be through an adapter into a bottle or vial or IV port.

FIG. 2 illustrates yet another embodiment of the valve device 2 in an exploded cross-sectional view of the valve device 2 which is adapted for suitable affixing to a bottle opening or throat. An upper female valve housing 36 is positioned above and in alignment for receiving lower valve assembly 38. Lower valve assembly 38 is aligned for affixing through locking rings 40 to a bottle 46 through bottle throat 48 and bottle throat locking ring receiver 52. As separated, a valve head 42 having valve head channels 44 is shown in the lower valve assembly 38 exposed and positioned for insertion into the upper valve housing chamber 56. The lower valve assembly 38 provides lower valve assembly housing 62 and lower valve assembly housing female chamber 64 for receiving upper valve housing 54 which in combination defines valve chamber 6 inclusive of valve 8 and valve spring means 10.

The exploded cross-sectional view of the valve device adapter suitable for affixing to a bottle throat shown in FIG. 2 can provide variations of the valve spring means 10 which are not shown. For example, the valve head 42 can be positioned at a first end of a support member which replaces the flexible valve spring means 10, said member being slidably mounted within the lower valve assembly for allowing valve head 42 travel in an up and down motion, the member being surrounded by for example either metal coil springs within the valve chamber 6 or with compressible elastomeric ring spring means also located in the valve chamber 6 as long as valve chamber 6 is sufficiently large enough in diameter to allow the function of these various spring means while avoiding blockage or significant blockage of liquid or fluid flow through the valve device to and from the bottle 46 and needle free syringe 22.

Figure 4:
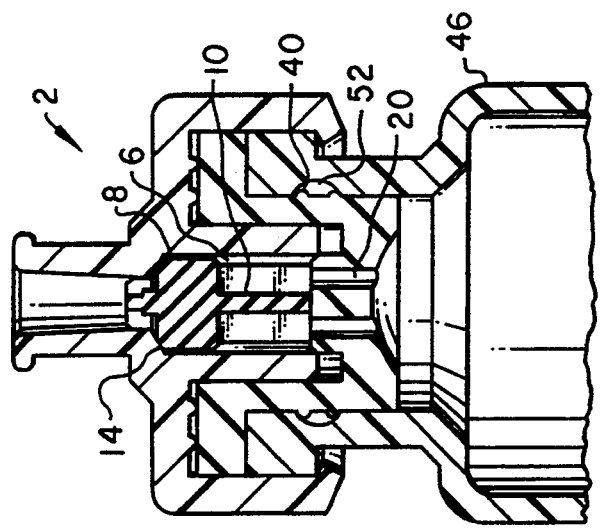
FIG. 4 is a cross-sectional view of the valve device and bottle throat of FIG. 3 in assembled relationship for use.
Figure 3:
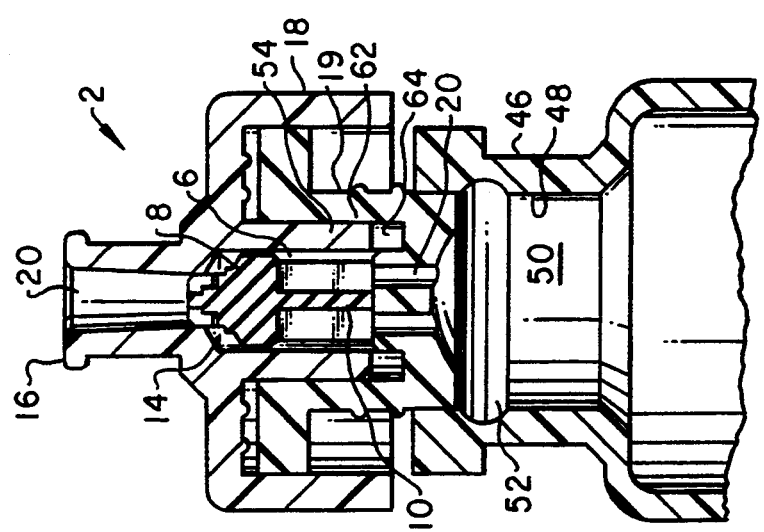
FIG. 3 is a cross-sectional view of the valve device and bottle throat of FIG. 2 in partial assembly position.

FIGS. 3, 4 and 5 are cross-sectional views, the valve device 2 positioned either in partial assembly as in FIG. 3 or fully assembled and locked in place position of the valve device 2 and bottle 46 and bottle throat 48 as in FIG. 4. In both FIGS. 3 and 4 the valve is in a closed position. In FIG. 5 a needle free syringe 22 is positioned in alignment for insertion of the needle free syringe male tip 24 into the valve device 2 female connector 16 where upon insertion of the needle free syringe male tip 24 will depress the valve 8 to a valve open position 32 (not shown). The insertion of the needle free syringe 22 male tip 24 maintains the valve 8 in a valve open position by luer lock or other attachment means which hold the needle free syringe 22 male tip 24 in a measured penetration of the valve female connector 16 until released. Upon release or removal of the needle free syringe 22 male tip 24, the valve 8 will again be forced to a closed position by valve spring means 10. Upon reaching a closed position, the valve seals the valve chamber from fluid flow in either direction by resting against the valve seat 14.

Figure 6:
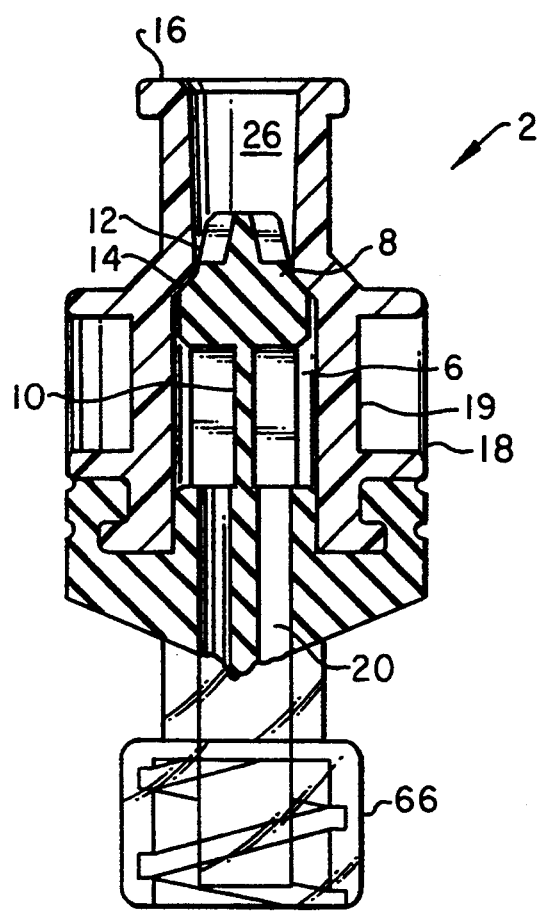
FIG. 6 is a cross-sectional view of the assembled valve device with a luer lock or screw adapter for affixing to a bottle throat or IV port.

FIG. 6 presents a cross-sectional view of the assembled valve device 2 with a luer lock or a screw adapter 66 for affixing to a bottle or IV port having the appropriate mating male member.

Figure 7:
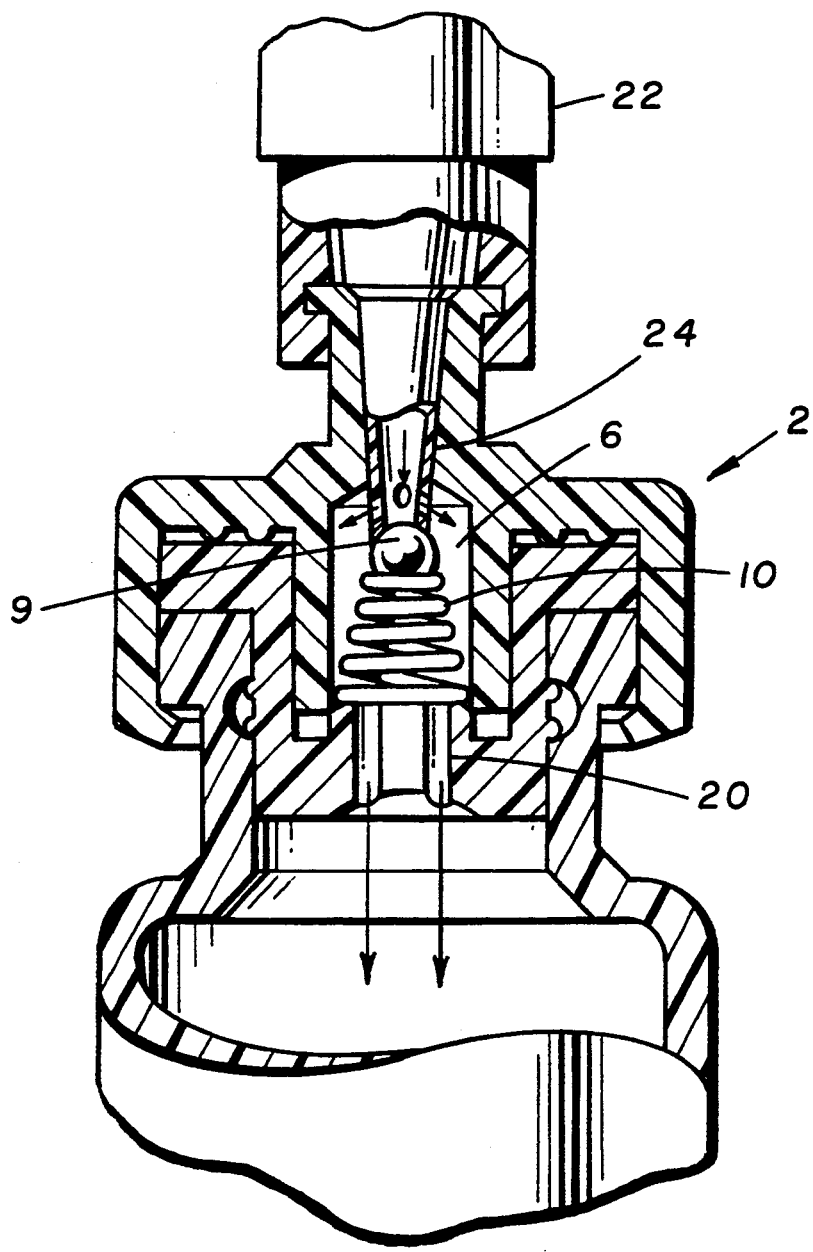
FIG. 7 is a cross-sectional view of another embodiment of the valve device showing a ball valve with the ball valve in an open position due to contact with a needle free syringe tip projection.

FIG. 7 presents a cross-sectional view of a ball valve device with the ball valve in an open position due to contact with a needle free syringe tip projection. The needle free syringe 22 tip 24 is shown in an inserted position into the valve device 2 where it is making contact with ball valve 9. Ball valve 9 is supported by spring means 10 within the valve chamber 6. Valve chamber 6 has passages 20 in open communication through an adapter into a bottle or vial or IV port.

In all of the figures, the valve device 2 provides a valve chamber 6 inclusive of valve 8 which is spring loaded by valve spring means 10 to force the valve 8 into a closure position upon removal of an external force applied generally through a needle free syringe 22 male tip 24. It is readily apparent that such activation, i.e. opening of valve 8, could be achieved by other projection means. When opened, valve 8 has a valve head 42 channels 44 which allow fluid communication between the valve chamber 6 and the needle free syringe male tip passage 26. In one embodiment, the valve spring means 10 is constructed of flexible fins generally extended in 90° angles which provide stable, slidable movement of the valve head 42 within the valve chamber 6. Even when the valve spring means 10 are compressed and the valve 8 is in valve open position 32, said compressed and distorted elastomeric spring means do not substantially restrict flow of fluids and liquids through the valve chamber.

In FIG. 5 the valve device 2 assembly as affixed to bottle 46 through bottle throat 48 through locking rings receiver 52 is shown separated from the needle free syringe male tip 24. The valve 8 is in a closed position until the needle free syringe male tip 24 makes contact with valve head 42 forcing compaction of the valve spring means 10. Upon removal of the needle free syringe 22 male tip 24, the valve spring means 10 force the valve 8 into valve closed position. In FIG. 1A the needle free syringe 22 metal tip 24 is in contact with valve head 24 in a penetrating position so that the valve head is moved away from the valve seat 14 thereby compressing the valve mean springs 10 until the tip is removed.

Various universal connector means can be utilized for both ends of the valve device 2 and can be constructed of readily accessible material such as plastic and the like. Generally such connector means are comprised of twist lock or luer lock means commonly utilized in the medical industry. It will be seen that the valve device apparatus and methods for use in the valve device can be performed with a minimum of health worker exposure and patient exposure to undesired needle sticks resulting from handling of needle-type syringes now utilized for transferring medicinal liquids from the vials and bottles to, for example, IV ports. Other uses of the valve device which have not been discussed will be really apparent to one practicing the art in view of the above descriptions and discussions of the disclosure and the following claims.

I claim:

1. A valve device for use in fluid transfer requiring a transfer from a needle free syringe having a barrel and a distal tip to a bottle having a throat, comprising:
   a unitary bottle throat adapter having valve means with internal spring means unitarily attached to said adapter and passage means permitting open communication between said syringe barrel and the bottle;
   said open communication being subject to said valve means contained in the bottle and bottle throat adapter;
   said valve means being closed by the internal spring means and adapted for displacement to an open position by contact with said needle free syringe distal tip.

2. A valve device in accordance with claim 1 wherein the device is suitable for liquid transfer through use of a needle free syringe for medical purposes.

3. A valve device in accordance with claim 2 wherein the valve means is comprised of a spring loaded piston valve within a valve chamber.

4. A valve device in accordance with claim 3 wherein the valve means is comprised of a flex member within a valve chamber.

5. A needle free valve device in accordance with claim 3 wherein the spring loaded piston valve has a head which seats against a sloped portion of an upper portion of the valve chamber, said valve head having channels which permit liquid flow around the valve when in open position.

6. A valve device for use in fluid transfer requiring a transfer from a needle free transfer syringe having a barrel and a distal tip to an IV port comprising a unitary IV port adapter having valve means with internal spring means unitarily attached to said adapter and passage means permitting open communication between said syringe barrel and the IV port, said open communication being subject to said valve means contained in the IV port and IV port adapter, said valve means closed by the internal spring means and adapted for displacement to an open position by contact with said needle free syringe distal tip.

7. A valve device in accordance with claim 6 wherein the valve means is comprised of a spring loaded piston valve within a valve chamber.

8. A valve device in accordance with claim 7 wherein the valve means is comprised of a flex member within a valve chamber.

9. A valve device in accordance with claim 7 wherein the spring loaded piston valve has a head which seats against a sloped portion of an upper portion of the valve chamber, said valve head having channels which permit liquid flow around the valve when in open position.

10. A two-piece valve device assembly for liquid transfer from a sealed container to a sealed liquid use system, comprising:

an upper housing defining a valve chamber in open communication with an open passage through an inserted needle free syringe tip for transfer of liquids to the syringe;

said upper housing defining a ring cavity around the valve chamber;

said cavity and chamber having a wall therebetween, the cavity for receiving a lower housing which is mounted with a spring loaded valve means;

said lower housing having preshaped means mateable with the ring cavity and an upper housing valve chambers circular wall;

said lower housing insertable into a bottled throat with locking rings on an exterior portion of the housing and having at least one open passage in communication between the valve chamber and the bottle throat;

said bottle throat having an internal slotted ring for receiving the locking rings; and said lower housing when positioned in the upper housing defining an outer receiving chamber between the upper housing outer housing wall and the outer lower chamber wall which receives the bottle throat wall configuration for securing the liquid valve device and adapter into the bottle throat.

11. A two-piece valve device in accordance with claim 10 wherein the device is suitable for liquid transfer through use of a needle free syringe for medical purposes.

12. A two-piece valve device in accordance with claim 10 wherein the valve means is comprised of a spring loaded piston valve within the valve chamber.

13. A two-piece valve device in accordance with claim 12 wherein the valve means is comprised of a flex member within the valve chamber.

14. A two-piece valve device in accordance with claim 12 wherein the spring loaded piston valve has a head which seats against a sloped portion of the valve chamber upper portion, said valve head having channels which permit liquid flow around the valve when in open position.

15. A one piece valve device assembly for liquid transfer use for medical purposes suitable for transferring fluid from a needle free syringe having a distal tip to a bottle having a throat, comprising:

said valve device assembly having a first end female connector in communication with an internal valve and valve chamber, said valve including a valve head unitarily attached to said valve chamber by spring means, said valve chamber in open communication through a second end bottle throat adapter for affixing the bottle to the valve device assembly with the bottle throat for two way transfer of liquid to and from the bottle by said needle free syringe, said syringe mateable through said distal tip with the valve assembly first end connector and when inserted, the syringe distal tip opens the valve by compression of the valve head and the internal valve spring means.

16. A valve device assembly according to claim 15 wherein the second end adapter connects with an IV port.

17. A valve device assembly according to claim 15 wherein the needle free syringe tip is lockable in place upon insertion by luer lock means.

18. A valve device assembly according to claim 15 wherein the bottle throat adapter is comprised of a luer lock bottle connector.

19. A valve device assembly according to claim 15 wherein the valve is comprised of a spring loaded piston valve within the valve chamber.

20. A valve device assembly according to claim 15 wherein the valve is comprised of a flex member within the valve chamber.

21. A valve device assembly according to claim 20 wherein the spring loaded piston valve has a head which seats against a sloped portion of a valve chamber upper portion, said valve head having channels which permit liquid flow around the valve when in open position.

22. A method for transferring liquid through use of a needle free syringe having a distal tip and barrel, comprising:

inserting the distal tip of the needle free syringe into a first valve means;

contacting the valve means and forcing the valve means to an open position allowing open communication between a barrel of the syringe through a syringe hollow distal tip, a valve chamber and attached medical structure containing liquid;

filling the needle free syringe barrel;

withdrawing the needle free syringe distal tip from contact with the valve means which allows the valve means to be closed by spring means; and inserting the needle free syringe distal tip into a second valve means attached to a second medical structure for insertion of the withdrawn liquid through the second valve means having a spring loaded valve which opens upon penetrating contact of the syringe distal tip.

23. A method according to claim 22 wherein the liquid is a body fluid.

* * * * *